United States Patent
Siepser

(10) Patent No.: US 9,867,735 B2
(45) Date of Patent: Jan. 16, 2018

(54) OPTHALMIC DEVICE FOR CELL REMOVAL

(71) Applicant: Katena Products, Inc., Denville, NJ (US)

(72) Inventor: Steven Bert Siepser, Wayne, PA (US)

(73) Assignee: Katena Products, Inc., Denville, NJ (US)

( * ) Notice: Subject to any disclaimer, the term of this patent is extended or adjusted under 35 U.S.C. 154(b) by 0 days.

(21) Appl. No.: 14/644,198

(22) Filed: Mar. 10, 2015

(65) Prior Publication Data

US 2016/0030241 A1    Feb. 4, 2016

Related U.S. Application Data

(60) Provisional application No. 61/950,534, filed on Mar. 10, 2014.

(51) Int. Cl.
*A61F 9/007* (2006.01)

(52) U.S. Cl.
CPC ................ *A61F 9/00736* (2013.01)

(58) Field of Classification Search
CPC .................................... A61F 9/00736
See application file for complete search history.

(56) References Cited

U.S. PATENT DOCUMENTS

| | | | | |
|---|---|---|---|---|
| 2,555,076 A * | 5/1951 | Crossley | ............... | A61B 17/50 606/107 |
| 3,508,547 A * | 4/1970 | Deuschle | ............. | A61C 19/063 604/1 |
| 5,147,369 A * | 9/1992 | Wagner | .................. | A61B 17/30 294/99.2 |
| 5,569,279 A * | 10/1996 | Rainin | ................ | A61F 9/00736 606/1 |
| 5,891,153 A * | 4/1999 | Peterson | ............. | A61F 9/00736 606/107 |
| 5,921,998 A * | 7/1999 | Tano | ................... | A61F 9/00736 606/161 |
| 7,326,220 B1 * | 2/2008 | Goldstein | ............ | A61B 17/221 606/107 |
| 2003/0135221 A1 * | 7/2003 | Sabet | ..................... | A61F 9/007 606/107 |
| 2005/0159758 A1 * | 7/2005 | Laks | .................. | A61F 9/00736 606/107 |
| 2008/0183199 A1 * | 7/2008 | Attinger | .............. | A61F 9/00736 606/161 |
| 2008/0195127 A1 * | 8/2008 | Bar-On | ................. | A61F 9/0133 606/166 |
| 2009/0171326 A1 * | 7/2009 | Hohla | ................. | A61F 9/00736 606/6 |
| 2012/0087970 A1 * | 4/2012 | Newman | ................. | A61F 9/013 424/427 |
| 2015/0216722 A1 * | 8/2015 | Choate | ............... | A61F 9/00772 606/162 |

* cited by examiner

*Primary Examiner* — Shaun L David
(74) *Attorney, Agent, or Firm* — Fredrikson & Byron, P.A.

(57) ABSTRACT

In described embodiments, an ophthalmic device provides for cell removal. In one embodiment, the ophthalmic device is introduced into the eye to remove cells on the underside of the anterior capsular membrane and the posterior capsular surface that can grow and block vision in an eye following cataract surgery. The ophthalmic device includes a disk with either a cleaning edge or tacky substance, and is inserted via shaft, the shaft coupled directly to the disk and forming a cannula, or optionally coupled to the disk with a separate cannula there between.

10 Claims, 2 Drawing Sheets

OPTHALMIC DEVICE FOR CELL REMOVAL

CROSS-REFERENCE TO RELATED APPLICATIONS

This application claims the benefit of the filing date of U.S. provisional application No. 61/950,534 filed Mar. 10, 2014, the teachings of which are incorporated herein in their entireties by reference.

BACKGROUND

Posterior capsular opacification (PCO) is a frequent complication of cataract surgery. PCO occurs because lens epithelial cells remaining after cataract surgery have grown on the capsule. In some cases, if the condition progresses significantly, the patient's vision may be worse than it was before cataract surgery. Therefore, improved tools for removing lens epithelial cells from the underside of the anterior capsular membrane and the posterior capsular surface are needed.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Described embodiments provide an ophthalmic device for cell removal. The ophthalmic device, termed herein as a "Squeegee" is introduced into the eye to remove cells on the underside of the anterior capsular membrane and the posterior capsular surface that can grow and block vision in an eye following cataract surgery.

BRIEF DESCRIPTION OF THE DRAWING FIGURES

Other aspects, features, and advantages of the present invention will become more fully apparent from the following detailed description, the appended claims, and the accompanying drawings in which like reference numerals identify similar or identical elements.

DETAILED DESCRIPTION

Figure 1:
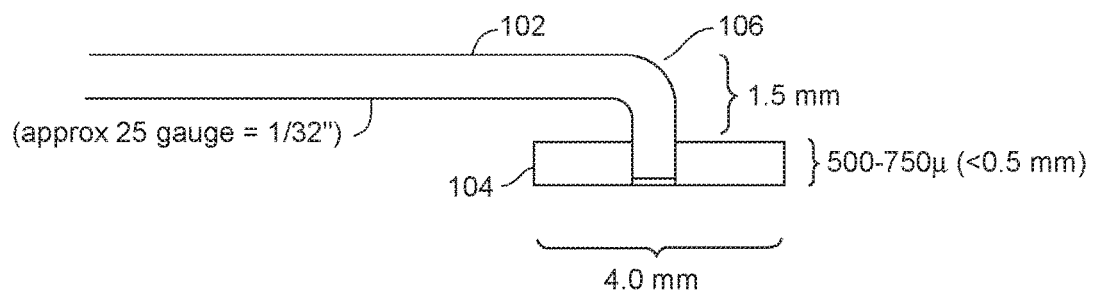
FIG. 1 shows an exemplary configuration for a Squeegee in accordance with an embodiment.

Embodiments described herein provide for an ophthalmic device for cell removal. The ophthalmic device, termed herein as a "Squeegee" is introduced into the eye to remove cells on the underside of the anterior capsular membrane and the posterior capsular surface that can grow and block vision in an eye following cataract surgery.

The Squeegee is a microsurgical instrument that is a fine, disk like, petalloid, cruciate or triad shaped, edged or flat cleaner. In one configuration the sharp edged plastic, silicone, or metal device is designed to allow for a 360 degree cleaning action without re-positioning of the Squeegee inside the eye or removing it to make an additional approach to areas not readily accessible by other techniques. It is a disk like, or other shaped device that is placed on the tip of a microsurgical cannula or surgical steel, Titanium, shaft, composite or plastic rod like structure to support the disk so it can be used in any direction. This cannula has an ability to be inserted into spaces slightly smaller than the diameter of the disk due to the ability of the disk or arms to flex in some design configurations.

The cannula is bent from several degrees to over 90 degrees to create more purchase for the disk and make the orientation more favorable for its cleaning action. The shaft can have multiple bends to ease entry and control or be configured for various incision sites. The tip of the cannula, or rod like substance part of the device is finished in such a way that the tip can be inserted in the collar like portion of the disk. This cannula might be fashioned in several ways to be self-retaining or glued into position if needed. The cannula or shaft can be formed into a "nail like head" that is subsequently cast into the rubber, plastic, silicone or composite disk to increase stability, retention and control. Some embodiments might be configured to accommodate irrigation into the space the Squeegee is working to keep structures under pressure and in position or used for suction to help with the removal of unwanted debris or cells.

The preferred material for the shaft might be that which would be best mated with a hub that commonly fits into a syringe or microsurgical handle such as used in irrigation of the eye or is easily mounted on existent surgical handles. This shaft is similar in dimensions to the connectors in intravenous (IV) tubing or Luer Locks commonly used on syringes to retain this hub that connects to a needle, in this case a hollow cannula or surgical quality steel or the like substance that flexes but requires substantial force to break, such that it does not break during normal use. This shaft is then bent at an angle to ease insertion into the eye and positioning of the working end of the device. The shaft can be an integral part or be elongated and thickened into a handle according to materials used and manufacturing process. The disk itself is best made of a somewhat sticky plastic or silicone that deforms for entry but is stiff enough to present the edge to the surfaces that are to be swept of cells and debris.

In the ocular application, the dimensions can be widely varied on the microscopic scale. The total diameter of the disk can be from 2 mm (or less) up to 11 mm total diameter to speed the cleaning action. The ideal diameter is about 4 mm so as to allow 2 mm of cleaning area and removing all the anterior capsule epithelial cells. This is the key action as to allow the device to Squeegee off these cells and leave a clean bare membrane free of cells or debris. The posterior capsule often has adherent cortex and this material can be swept away with the underside of the Squeegee disk. The disk can have a 100-500 micron edge, or no edge at all, as certain materials are tacky enough to remove debris without having any particular edge design.

FIG. 1 shows an exemplary configuration for a Squeegee in accordance with an embodiment. As shown in FIG. 1, the Squeegee comprises shaft 102, which might be approximately 25 gauge (about the thickness of a paperclip) and disk 104, which is shown with diameter of 4 mm and thickness of about 500-750μ. Cannula 106 is shown bent approximately 90 degrees and height of about 1.5 mm above disk 104.

Figure 2:
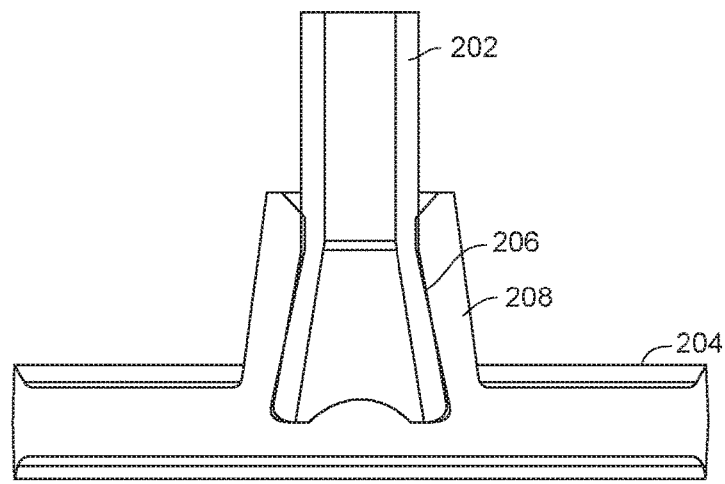
FIG. 2 shows another exemplary configuration for a Squeegee.
Figure 3:
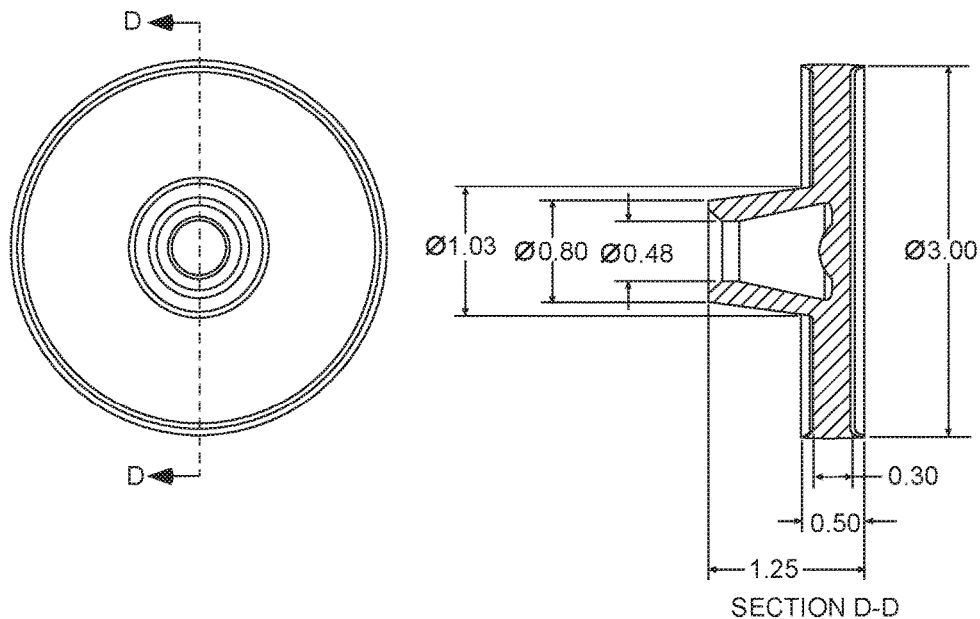
FIG. 3 shows a disk for the exemplary configuration of FIG. 2.
Figure 4:
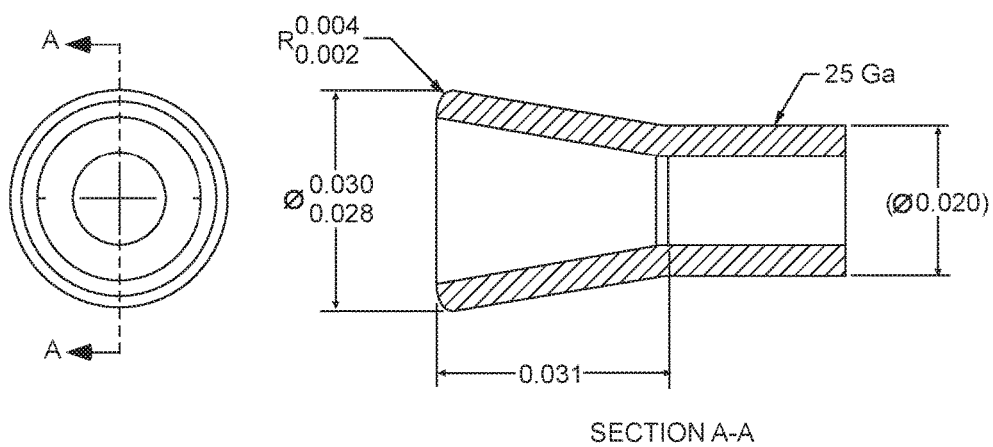
FIG. 4 shows a cannula flare detail for the configuration of FIG. 2.

FIG. 2 shows another exemplary configuration for a Squeegee. As shown, the Squeegee includes a cannula 202 having flared end 206. Flared end 206 is shaped to fit into hub 208 of disk 204. FIG. 3 shows a disk implementation detail and FIG. 4 shows a cannula flare detail for the exemplary configuration of FIG. 2, with dimensions in mm.

The device might be easily provided by employing present manufacturing and related quality standards well known in the art. The device might preferably be 3-D printed, machined, or cast using the various methods of model/mold techniques to provide the master mold for casting, injection molding, or stamping. The device-specific details can be molded, or machine cut, using freezing techniques to allow production of finer details. The device-specific details can also be laser cut, pressed, stamped, heat deformed, molded, or compressed. The metal, plastic or hardened silicone carrier can be fluted, headed by using machining techniques, pressed into place, shrink tightened, glued, cast or clamped into position. The entire part or pieces are cleaned and sterilized using various methods from steam sterilization, Gas, or Gamma ray among the commonly known choices. The Squeegee can be manufactured as a single use disposable or re-usable device according to medical guidelines of the institution or country where it will be used.

The Squeegee can be used for multiple types of surgery, mechanical applications and industry use where cleaning action is needed in enclosed spaces where access is limited but the area that needs cleaning is larger than the entry site. For example, the device can be introduced through a trocar in abdominal surgery to be used to remove cells and debris from membranes and biological surfaces. It also can be used in some manufacturing processes where mechanical cleaning would be more effective than other methods. For example it can be made of a size and shape that would better clean the inside surfaces of a bottle using the neck for entry. In another iteration of an intra-vascular application it can be placed at the end of an intra-vascular catheter and used to wipe away unwanted cells, membranes of debris. For one application it can be used to assist in endocardial stripping for atrial fibrillation where the conducting membrane is stripped from underlying structures. By providing a 360 degree cleaning surface it is more effective than straight line Squeegee and it's round or oval shape can be applied in various and multitudinous applications.

Reference herein to "one embodiment" or "an embodiment" means that a particular feature, structure, or characteristic described in connection with the embodiment can be included in at least one embodiment. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Although the subject matter described herein may be described in the context of illustrative implementations to process one or more computing application features/operations for a computing application having user-interactive components the subject matter is not limited to these particular embodiments. Rather, the techniques described herein can be applied to any suitable type of user-interactive component execution management methods, systems, platforms, or apparatus.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Also for purposes of this description, the terms "couple," "coupling," "coupled," "connect," "connecting," or "connected" refer to any manner known in the art or later developed in which energy is allowed to be transferred between two or more elements, and the interposition of one or more additional elements is contemplated, although not required. Conversely, the terms "directly coupled," "directly connected," etc., imply the absence of such additional elements.

Directional terms may be used in the specification and claims to describe portions of exemplary embodiments (e.g., upper, lower, left, right, etc.). These directional definitions are merely intended to assist in describing and claiming the embodiments and are not intended to limit the embodiments in any way.

It will be further understood that various changes in the details, materials, and arrangements of the parts which have been described and illustrated in order to explain the nature of described embodiments may be made by those skilled in the art without departing from the scope as expressed in the following claims.

We claim:

1. An ophthalmic device for cell removal from a patient's eye, the ophthalmic device comprising:
  a disk comprising a cleaning surface and a hub, wherein the hub has a first portion, a second portion, an inner diameter that increases along a first length from the first portion to the second portion, and a base surface having a first elevation and a second elevation, the second elevation being different from the first elevation;
  a shaft having a first end and a second end, the second end of the shaft coupled to the hub by a cannula, and the first end of the shaft configured to be mounted to a handle, wherein the cannula has a third portion, a fourth portion, an increased diameter along a second length from the third portion to the fourth portion, and an end portion, and wherein the second length of the cannula is received within the first length of the hub, the end portion of the cannula positioned at the first elevation of the base surface of the hub, and the second elevation of the base surface of the hub extends into the cannula, wherein the disk is configured to be introduced into the patient's eye by the shaft, the ophthalmic device configured to remove cells on the underside of an anterior capsular membrane of the patient's eye and a posterior capsular surface of the patient's eye.

2. The ophthalmic device of claim 1, wherein the cleaning surface comprises at least one of a cleaning edge and a tacky substance.

3. The ophthalmic device of claim 1, wherein the shaft is coupled directly to the disk thereby forming the cannula.

4. The ophthalmic device of claim 1, wherein the cannula is formed by a separate cannula disposed between the shaft and the disk.

5. The ophthalmic device of claim 1, wherein the shaft comprises a substantially 90 degree bend, the bend disposed closer to the second end of the shaft than the first end of the shaft.

6. The ophthalmic device of claim 1, wherein the cleaning surface of the disk is configured to flex.

7. The ophthalmic device of claim 1, wherein the hub defines an opening for receiving the second length of the cannula, the opening terminating at the base surface of the hub, wherein the opening defines the inner diameter of the hub that increases along the first length from the first portion to the second portion and includes a third length that includes a decrease of the inner diameter of the hub.

8. The ophthalmic device of claim 1, wherein the hub includes an outer diameter that increases at a constant rate along the first length.

9. The ophthalmic device of claim 1, wherein the hub defines an opening for receiving the second length of the cannula, wherein the opening beginning at a proximal end of the hub has a third length that includes a decrease of the inner diameter of the hub, wherein the third length terminates at a fourth length of the hub that is of a constant inner diameter, and wherein the fourth length terminates at the first length.

10. The ophthalmic device of claim 1, wherein the hub is defined by a continuous surface, and wherein the hub defines an opening extending from a proximal end of the hub to the base surface of the hub, the opening of the hub being formed by a space between the continuous surface.

* * * * *